May 29, 1973 C. H. LEE Plant Pat. 3,349

RAPHIOLEPIS PLANT

Filed Oct. 7. 1971 2 Sheets-Sheet 1

INVENTOR.
Charles H. Lee
BY
G. Gordon Angus
Donald S. Mon
Attorneys

RAPHIOLEPIS PLANT

Filed Oct. 7. 1971 2 Sheets-Sheet 2

INVENTOR.
Charles H. Lee
BY
G. Gordon Angus
Donald E. Moth
Attorneys

United States Patent Office

Plant Pat. 3,349
Patented May 29, 1973

3,349
RAPHIOLEPIS PLANT

Charles H. Lee, Azusa, Calif., assignor to Monrovia Nursey Company, Azusa, Calif.

Filed Oct. 7, 1971, Ser. No. 187,583
Int. Cl. A01h *5/00*
U.S. Cl. Plt.—54 1 Claim

ABSTRACT OF THE DISCLOSURE

A new variety of Raphiolepis plant characterized by exceptionally large coriaceous leaves and a profusion of very large pale pink flower clusters.

This invention relates to a new and distinct variety of Raphiolepis plant discovered by me.

At the time of my discovery, I found it as a chance seedling growing in a bed of *Raphiolepis indica* "Enchantress," where it was distinguished from all the other Raphiolepis plants in the bed by the relatively great size of its branches and foliage. The actual parentage of this seedling is unknown.

The new variety of Raphiolepis plant is characterized by its exceptionally large branches and large coriaceous leaves and the profusion of very large pale pink flower clusters.

The accompanying drawings show a typical specimen of the plant according to this invention and blooms and foliage thereof, and are depicted in color as nearly true as it is reasonably possible to make the same in a color photograph of this character, in which.

Figure 1:
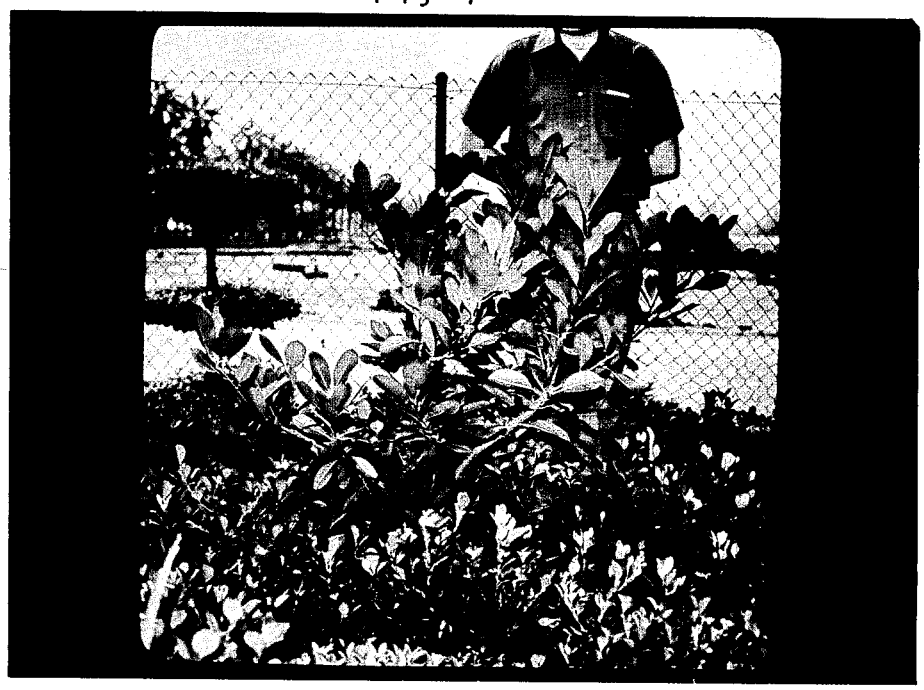
FIG. 1 is a side view of the plant without blooms.
Figure 2:
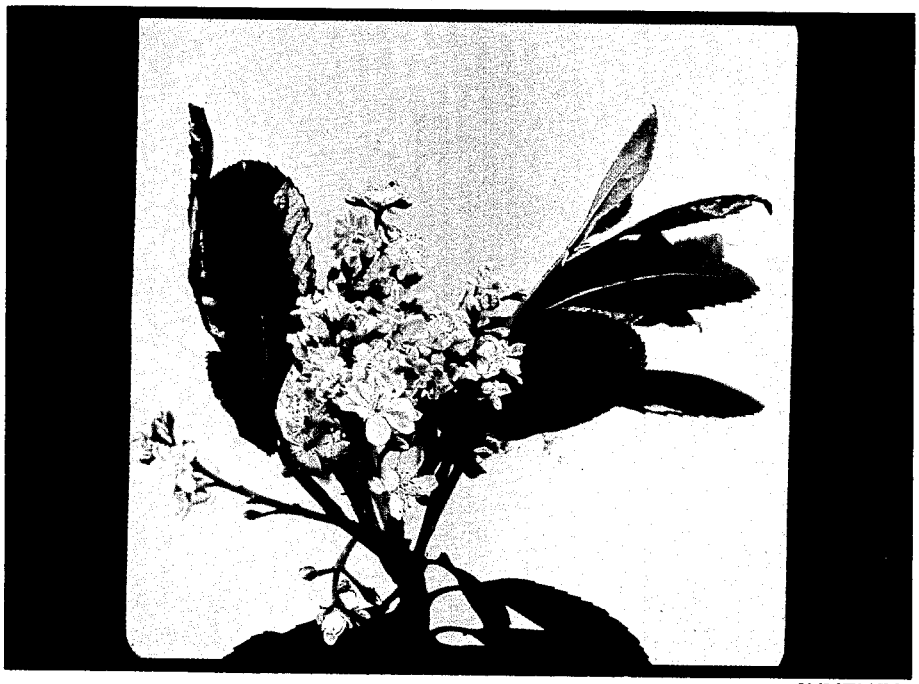
FIG. 2 is a close-up view of a head of flowers of the plant, including adjacent foliage.
Figure 3:
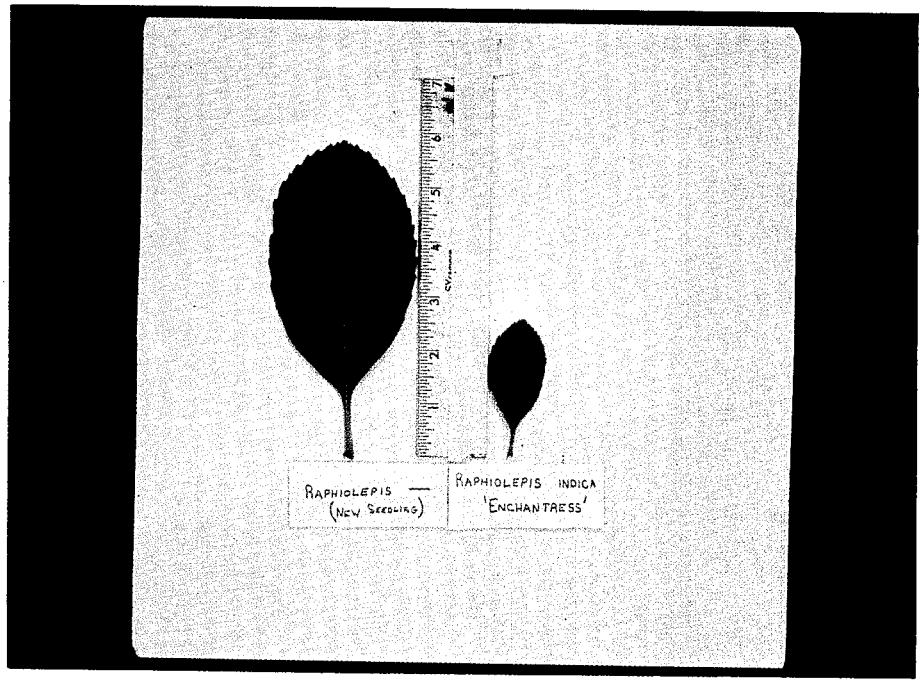
FIG. 3 is a view of a single leaf of the plant showing its actual size, placed adjacent a typical leaf of a *Raphiolepis indica* "Enchantress."

The following is a detailed description of my new Raphiolepis variety with color terminology in accordance with the Royal Horticultural Charts.

Locality where discovered and grown: Azusa, California.

Propagation: The plant is reproduced from grafts and cuttings and holds its distinguishing characteristics through succeeding propagations in this manner. It is not expected to reproduce true from seed.

Growth habit: The plant emerges from the soil on a single stem and exhibits a slightly upright to spreading habit. Branches are somewhat arching and are extremely dense.

Branches: The young shoots are slightly tomentose and the bark appears reddish brown to green. The older shoots are greyish-brown, with somewhat scurfy bark. Both the young and old wood are very brittle. The branches appear very sturdy with calipers increasing rapidly with age.

Foliage: The leaves are alternate and conspicuously larger than any other variety of Raphiolepis, the leaves being 5¾" to 6" long and 2¼" to 2¾" wide. The shape of the leaf is obovate to elliptic, with a petiole ¾" to ⅞" long. The midrib is prominent on both sides of the blade, while the smaller veins are prominent beneath. The margin is closely crenate to serrate. The base is obtuse and the apex is broadly acute. The color of the upper surface is Ivy Green 0001060, with a shiny appearance. The underside is Willow Green 000862/1 with a mottled effect created by the darker veins.

Flowers: The flowers are borne in very large clusters. Each flower has from five to twelve petals, each being about 3/16" wide and 5/16" long. Their colors vary from Dawn Pink $_5$23/2 to $_5$23, and their shapes vary from lanciolate to obovate or spatulate. Each flower has numerous stamens and one pistil with three styles fused at the base. There five sepals whose margins are ciliate.

I claim:

1. A new and distinct variety of the genus Raphiolepis, the novelty of the plants being characterized by the exceptionally large coriaceous leaves and the profusion of very large pale pink flower clusters.

No references cited.

ROBERT E. BAGWILL, Primary Examiner

UNITED STATES PATENT OFFICE

CERTIFICATE OF CORRECTION

Patent No. Plant 3349 Dated May 29, 1973

Inventor(s) CHARLES H. LEE

It is certified that error appears in the above-identified patent and that said Letters Patent are hereby corrected as shown below:

Column 2, line 21

Change "closely" to --coarsely--

Column 2, line 23

Change "0001060" to --ooo1060--

Column 2, line 24

Change "000862/1" to ooo862/1--

Column 2, line 29

Change "$_5$23/2 to $_5$23" to --523/2 to 523--

Column 2, line 30

Change "lanciolate" to --lanceolate--

Column 2, line 32

After "There" insert --are--

Signed and sealed this 18th day of December 1973.

(SEAL)
Attest:

EDWARD M.FLETCHER,JR.
Attesting Officer

RENE D. TEGTMEYER
Acting Commissioner of Patents